United States Patent [19]
Raible

[11] Patent Number: 4,512,761
[45] Date of Patent: Apr. 23, 1985

[54] BODY IMPLANTABLE CONNECTOR

[75] Inventor: Donald A. Raible, Irvine, Calif.

[73] Assignee: Bentley Laboratories, Inc., Irvine, Calif.

[21] Appl. No.: 539,623

[22] Filed: Oct. 6, 1983

Related U.S. Application Data

[63] Continuation of Ser. No. 292,846, Aug. 14, 1981, abandoned.

[51] Int. Cl.³ .............................................. A61B 19/00
[52] U.S. Cl. ........................................ 604/8; 604/175; 604/905; 128/1 R
[58] Field of Search .......................... 604/8, 175, 905; 128/1 R, 334 R, 335; 427/2; 3/1, 1.4

[56] References Cited

U.S. PATENT DOCUMENTS

| | | | |
|---|---|---|---|
| 3,276,448 | 10/1966 | Kronenthal | 3/1.4 X |
| 3,877,462 | 4/1975 | Bucalo | 128/1 R |
| 3,951,132 | 4/1976 | Bucalo | 128/1 R |
| 4,319,363 | 3/1982 | Ketharanathan | 427/2 X |

Primary Examiner—George F. Lesmes
Assistant Examiner—Nancy A. B. Swisher
Attorney, Agent, or Firm—Lyon & Lyon

[57] ABSTRACT

A body implantable connector to replace a portion of a patient's body fluid or solid carrying conduit and to connect this body conduit to a vascular implant device in order to provide access to the body conduit external from the body. The connector includes a tubular member expanded along its length in order to form a bulbous portion; a side port is provided for connection to the vascular implant device at the approximate midpoint of the tubular member bulbous portion.

12 Claims, 2 Drawing Figures

BODY IMPLANTABLE CONNECTOR

This application is a continuation of Ser. No. 292,846, filed Aug. 14, 1981, now abandoned.

BACKGROUND OF THE INVENTION

The present invention relates to a body implantable connector to facilitate the installation of a vascular implant device.

There are a number of situations in which it is necessary to provide for fluid communication with the vascular system. For example, patients suffering from kidney failure require the dialysis of their blood by means external from the body. Blood containing toxic substances, such as urea, uric acid, creatine, phosphorus and calcium, must be removed from the blood system, treated and then returned to the patient. Patients requiring such blood dialysis require treatment at least two or three times per week. Patients suffering from the hypoalimentation require a device for providing access to the body's vascular system on at least a daily basis.

One prior method of providing fluid communication with the vascular system involved the insertion of a needle into an artery from which blood to be treated was taken and the insertion of a needle into a patient's vein for blood return. Such a method proved unsatisfactory due to the difficulty in providing for the healing of the artery upon removal of the needle and the trauma produced by the repeated needle insertions. Such shortcomings led to the development of external and, later, internal shunts.

An external shunt involves the insertion of tubes, such as those made of Teflon, into an artery and an adjacent vein in a limb and providing an external communication or shunt between the tubes, which extend from the body of the patient. The shunt between the tubes is required in order to provide flow through the tubes during that period of time that access is not required for blood treatment. Where such circulating blood flow not provided, a blood or clot or thrombus could form as would be the case if the tubes were simply capped creating a static blood volume when the tubes were not in use. Dialysis, for example, is accomplished by connecting the arterial and venous tubing to a suitable dialysis unit. However, such a configuration traumatizes the skin adjacent the Teflon tubes and a path is provided through the skin for infection to enter the patient's body. Furthermore, even with external shunts, blood clots sometimes form within the tubes and create a health hazard to the patient.

The disadvantages of external shunts led to the development of the internal shunt. An internal shunt is performed by joining, within a body, openings between an artery and an adjacent vein, thereby forming a fistula. One or two needles are then inserted into the fistula in order to achieve communication with the patient's vascular system. The patient suffers major discomfort and pain each time the needles are inserted into the fistula. Moreover, the continous intrusion into the fistula causes it to become layered with scar tissue which ultimately prevents further intrusion, thus requiring the formation of another shunt.

Both the internal and external shunts increase the loading on the patient's heart due to the joining of the artery to a vein having a lower pressure, thereby lowering the artery's pressure, and requiring the heart to attempt to regain the original arterial blood pressure. Further, in many cases, the reduced circulation in the distal portion of the limb wherein the shunt is effected impairs the adequate perfusion of blood.

A vascular implant device of the type for which the present invention facilitates the installation hereof is, for example, the valved implant device disclosed in issued U.S. Pat. No. 4,164,221, issued Aug. 14, 1979 of which the inventor of this invention was a coinventor and hereby incorporated by reference.

DESCRIPTION OF PREFERRED EMBODIMENTS

Figure 1:
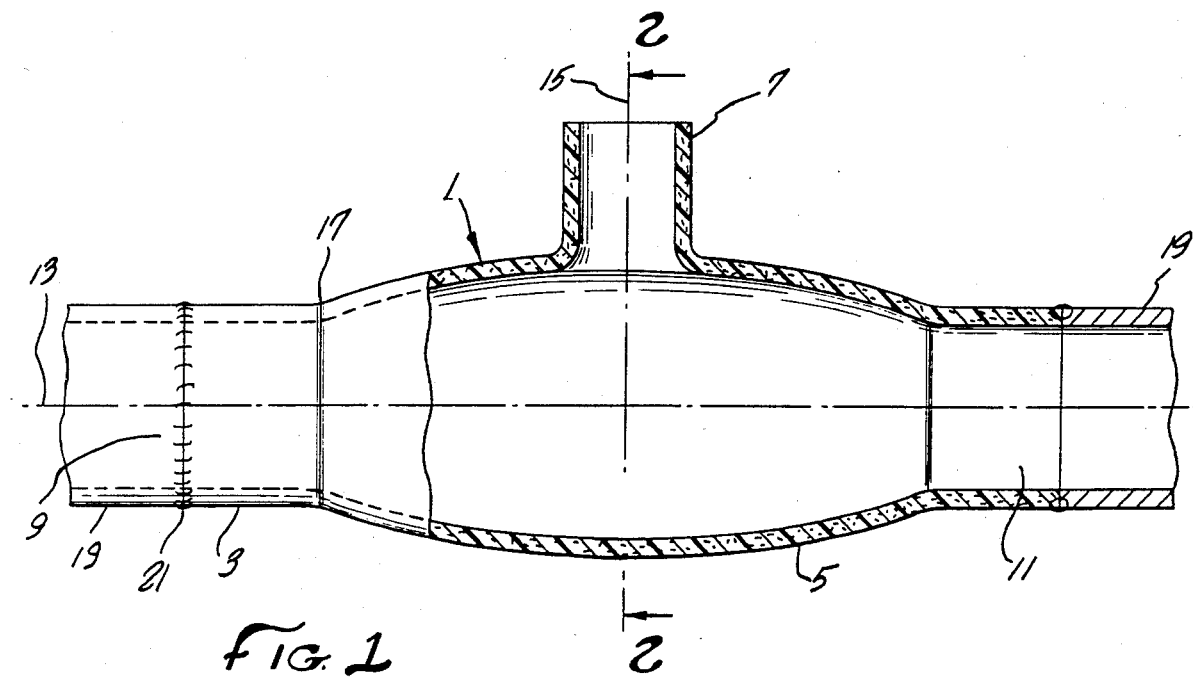
FIG. 1 is a pictorial view illustrating the present invention.
Figure 2:
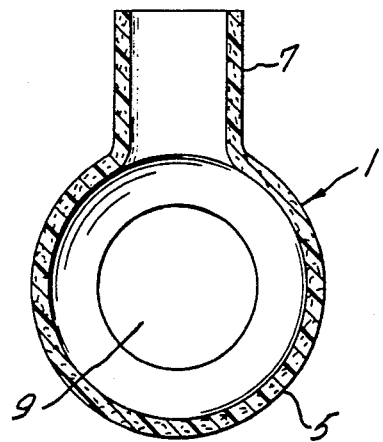
FIG. 2 is a cross-sectional view taken about 2—2 of FIG. 1.

Referring to FIG. 1, a body implantable connector, generally refered to as 1, is shown. The connector 1 is adapted to replace a portion of a patient's internal body fluid or solid carrying conduit such as blood vessel 19. The connector 1 is connected to the remaining body conduit 19 means of annular suture 21, or the like. In an alternate embodiment to this "end to end" connection, the connector 1 may be "side to side" wherein, for example, the side of a vein is connected to the side of an artery.

Connector 1 includes a tubular member 3 having an increased diameter bulbous portion 5. A side port 7 is provided at the approximate midpoint of the bulbous portion 5 of the tubular member 3. The tubular member 3 preferably includes inlet 9 and outlet 11 of substantially cylindrical cross-section and having a common center line 13. The side port 7 is also preferably of cylindrical cross-section, having a centerline 15 which is substantially perpendicular to the common centerline 13 of inlet 9 and outlet 11 of tubular member 3.

The bulbous portion 5 preferably has a partial elliptical contour, the elliptical contour being truncated at its ends at the point 17 of diameter expansion from the diameter of tubular member 3 to the diameter of the bulbous portion 5. Preferably the diameter at the midpoint of the bulbous portion 5 is between about one and one-half to two times the diameter of the tubular member 3 prior to the diameter expansion at point 17. In addition, as shown in FIG. 1, it is preferable that the major axis of the elliptical bulbous portion 5 be approximately two times the minor axis of the elliptical bulbous portion 5.

The connector 1 is preferably of unitary construction, being fabricated of a grafting material which is formed, for example, from Dacron, an E. I. duPont de Nemours & Company product of polyester fiber, or "impra graft", a trademarked product made from polytetrafluoroethylene. In a preferred embodiment at least a portion of the grafting material from which connector 1 is made is coated with collagen.

The side port 7 of connector 1 is adapted to receive therewithin an end portion of a vascular implant device such as that of U.S. Pat. No. 4,164,221, hereby incorporated by reference.

What is claimed is:

1. A connector to replace a portion of the patient's internal body fluid or solid carrying conduit adapted to connect said body conduit to a vascular implant device for providing external access to said body conduit comprising:

a hollow tubular member of a grafting material, a portion of said tubular member being of expanded diameter to form a hollow bulbous portion positioned along the length of said tubular member, said bulbous portion being of a grafting material and being defined as having a partial elliptical contour, the elliptical contour being elongated substantially along a common center line between an inlet and an outlet to the hollow tubular member, truncated at its ends at the point of diameter expansion from the diameter of said tubular member to form said bulbous portion; and a side port of a grafting material at the approximate midpoint of said tubular member bulbous portion.

2. The connector claimed in claim 1 wherein said tubular member is further defined as having a substantially cylindrical inlet and an outlet.

3. The connector claimed in claim 2 wherein said side port is of substantially cylindrical shape and has a centerline substantially perpendicular to the common centerline of said tubular member inlet and outlet.

4. The connector claimed in claim 1 wherein said tubular member and said side port are of a unitary construction.

5. The connector claimed in claim 4 wherein said grafting material is further defined as being a fibrous material at least partially coated with collagen.

6. The connector claimed in claim 1 wherein the lateral diameter of said connector at the midpoint of said bulbous portion is between about 1.5 and about 2.0 times greater than the diameter of said tubular member prior to the diameter expansion to form said bulbous portion.

7. A body implantable connector to replace a portion of a patient's internal body fluid or solid carrying conduit adapted to connect said body carrying conduit to a vascular implant device for providing external access to said body conduit comprising:

a hollow, tubular member of grafting material, truncated at its ends said tubular member being expanded to form a bulbous portion of partially elliptical contour along the length of said tubular member said bulbous portion being of grafting material; and a side port, of unitary construction with said tubular member and of grafting material, said side port being positioned at the approximate midpoint of said bulbous portion diameter, said bulbous portion having a lateral diameter at the midpoint of said bulbous portion, as measured along the centerline of said side port, of between about 1.5 and about 2.0 times greater than the diameter of said tubular member prior to the diameter expansion to form said bulbous portion.

8. The connector claimed in claim 7 wherein said grafting material is further defined as being a fibrous material having at least a portion of the exterior thereof coated with collagen.

9. The connector claimed in claim 7 wherein said tubular member is further defined as having a substantially cylindrical inlet and an outlet, said cylindrical inlet and outlet having a common centerline.

10. The connector in claim 9 wherein said side port is of substantially cylindrical shape and has a centerline substantially perpendicular to the common centerline of said tubular member inlet and outlet.

11. A connector to replace a portion of a patient's internal body fluid or solid carrying conduit adapted to connect said body conduit to a vascular implant device for providing external access to said body conduit comprising:

a hollow, tubular member of grafting material, truncated at its ends said tubular member being expanded to form a bulbous portion of partially elliptital contour along the length of said tubular member, said bulbous portion being of polyester fiber; and a side port, of unity construction with said tubular member and of polyester fiber, said side port being positioned at the approximate midpoint of said bulbous portion diameter, said bulbous portion having a lateral diameter at the midpoint of said bulbous portion, as measured along the center line of said side port, of between about 1.5 and about 2.0 times greater than the diameter of said tubular member prior to the diameter expansion to form said bulbous portion, and the bulbous portion having a substantially elliptical shape, the major axis being along the length of the tubular member and the minor axis passing through the side port, the major axis being about two times greater than the minor axis.

12. A method of connecting a portion of a patient's internal body fluid or solid carrying conduit by a vascular implant device by connecting the conduit together through said vascular implant device and for providing external access to said body conduit comprising:

connecting a hollow tubular member, truncated at its ends of a grafting material, and having a portion of said tubular member of expanded diameter to form a hollow bulbous portion of partially elliptical contour along the length of said tubular member, at the ends of the tubular member with the conduit; and providing external access through a side port connecting with the tubular member, said side port being of a grafting material, and being at the approximate midpoint of said bulbous portion.

* * * * *